United States Patent [19]

Gramlich et al.

[11] Patent Number: 4,684,743

[45] Date of Patent: Aug. 4, 1987

[54] PREPARATION OF ALPHA-SUBSTITUTED β-DICARBONYL, β-CYANO-CARBONYL AND β-DICYANO COMPOUNDS

[75] Inventors: Walter Gramlich, Edingen-Neckarhausen; Klaus Halbritter, Mannheim; Gerd Heilen, Speyer, all of Fed. Rep. of Germany

[73] Assignee: BASF Aktiengesellschaft, Ludwigshafen, Fed. Rep. of Germany

[21] Appl. No.: 782,615

[22] Filed: Oct. 1, 1985

Related U.S. Application Data

[63] Continuation of Ser. No. 666,477, Oct. 30, 1984, abandoned, which is a continuation-in-part of Ser. No. 515,880, Jul. 21, 1983, abandoned.

[30] Foreign Application Priority Data

Jul. 22, 1982 [DE] Fed. Rep. of Germany ....... 3227388

[51] Int. Cl.[4] .................... C07C 69/38; C07C 120/00
[52] U.S. Cl. .................................. 558/374; 546/330; 546/335; 549/74; 549/76; 549/78; 549/79; 260/404; 260/405; 560/51; 560/82; 560/126; 560/127; 560/174; 560/190; 558/371; 558/372; 568/376; 568/390
[58] Field of Search ............................. 560/174, 190; 260/465.4, 464, 465.8 R, 465.1; 568/390; 558/373, 374, 371, 372

[56] References Cited

U.S. PATENT DOCUMENTS 3,839,418  10/1974  Hinton et al. ............ 260/410.9 R X

FOREIGN PATENT DOCUMENTS 2073109  9/1971  France .
1014273  12/1965  United Kingdom .

OTHER PUBLICATIONS

Schmall, et al.; C. A., 84, 84:105052f (1976).

Primary Examiner—Joseph Paul Brust
Attorney, Agent, or Firm—Keil & Weinkauf

[57] ABSTRACT

β-Dicarbonyl, β-cyanocarbonyl and β-dicyano compounds I

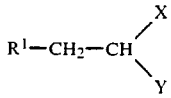

where $R^1$ is an organic radical, X and Y are $COOR^2$, $-CO-R^2$ or $-CN$ and $R^2$ is an organic radical, are prepared from $R^1-CHO$ (II) and $X-CH_2-Y$ (III) by reaction in the presence of a condensation catalyst, hydrogen and a hydrogenation catalyst, using an oxide or phosphate of Mg, Al, Ti, Zn or a rare earth metal as the condensation catalyst.

7 Claims, No Drawings

PREPARATION OF ALPHA-SUBSTITUTED β-DICARBONYL, β-CYANO-CARBONYL AND β-DICYANO COMPOUNDS

This application is a continuation of application Ser. No. 666,477, filed on Oct. 30, 1984 which is a continuation-in-part of Ser. No. 515,880 filed July 21, 1983 which applications have now been abandoned.

The present invention relates to an improved process for the preparation of α-substituted β-dicarbonyl, β-cyanocarbonyl and β-dicyano compounds of the general formula I

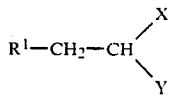   I where $R^1$ is hydrogen or an organic radical and X and Y are $-COOR^2$, $-CO-R^2$ or $-CN$, where $R^2$ is an organic radical, by reacting an aldehyde II

   II with a compound III

   III in the presence of a condensation catalyst, hydrogen and a hydrogenation catalyst.

The reaction of carbonyl compounds, including aldehydes II, with compounds III to give condensation products IV

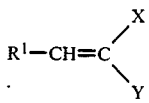   IV is generally known as the Knoevenagel reaction (cf. eg. "Organikum" VEB Deutscher Verlag der Wissenschaften, 1962, page 442). It is carried out in the liquid phase using various basic or acidic, usually homogeneous, catalysts and continuously removing the water of reaction formed.

German Published Application DAS 2,060,443 also discloses a procedure in which the Knoevenagel reaction is carried out in the presence of hydrogen and a hydrogenation catalyst so that compounds I are obtained directly.

Finally, British Pat. No. 1,014,273 discloses a procedure in which the aldol condensation of propionaldehyde is carried out under hydrogenating conditions by means of solid condensation catalysts, such as oxides and phosphates, including those proposed herein as condensation catalysts, to give 2-methylvaleraldehyde.

However, the condensation catalysts recommended for the Knoevenagel reaction are usually particularly suitable only for certain cases, so that different instructions and equipment are always required for the preparation of different compounds I. This obviously prevents efficient preparation of various compounds I which, as special products, are as a rule required in only limited amounts. Moreover, undesirable decarboxylation frequently takes place as a side reaction in the case of compounds III or I in which one or more of X and Y is $-COOR^2$, and finally, the use of homogeneous catalysts involves additional expenditure for removing them from the reaction mixtures formed.

It is an object of the present invention to remedy these deficiencies by means of a universally applicable heterogeneously catalyzed process without having to accept disadvantages such as undesirable side reactions or reduced yields.

We have found that this object is achieved and that the compounds I defined above are obtained in a technologically advantageous manner from the compounds II and III, also defined above, in the presence of a condensation catalyst, hydrogen and a hydrogenation catalyst by using an oxide or phosphate of magnesium, aluminum, titanium, zinc or a rare earth metal as the condensation catalyst.

We have also found that particularly good results are obtained using aluminum oxide as the condensation catalyst.

The solid catalyst components, ie. the hydrogenation catalyst and the condensation catalyst, can in principle be used separately, but it is usually advisable to use a mixed catalyst of from 0.1 to 50% by weight of the hydrogenating component and from 50 to 99.9% by weight of the condensing component.

If a noble metal, especially palladium, is used as the hydrogenation catalyst, the mixed catalyst is advantageously prepared conventionally, by processing the pulverulent condensation catalyst to a paste with an aqueous solution of a salt of one of the noble metals, the amount and concentration of the salt solution corresponding to the desired catalyst composition. This paste is then processed to catalyst particles, for example to beads from 1 to 10 mm in diameter or cylinders from 0.5 to 5 mm in diameter and from 1 to 10 mm in height, after which these particles are dried and heated at from 150° to 1,000° C. under a hydrogen atmosphere, whereupon the noble metal salt is reduced to the metal.

It is also possible to apply the paste to an inert carrier, eg. silicic acid, and to produce a supported catalyst in a conventional manner.

Palladium is the preferred hydrogenation catalyst and aluminum oxide is the preferred condensation catalyst. Of the $Al_2O_3$ modifications, those with a high specific surface area, ie. the γ-form (from 85 to 400 m²/g) and the η-form (from 100 to 600 m²/g), are particularly preferred. α-$Al_2O_3$ (from 40 to 70 m²/g) is also suitable but requires somewhat longer reaction times.

Particularly suitable oxides and phosphates of rare earth metals are those of cerium, praseodymium and neodymium. A mixture of from 1 to 10% by weight of compounds of rare earth metals and from 90 to 99% by weight of another oxide or phosphate conforming to the above definition, in particular $Al_2O_3$, is preferably used.

In principle, any desired amount of catalyst can be used for the reaction according to the invention, since it only influences the rate of reaction. However, for technological reasons, the amount should advantageously not exceed 0.4 kg per kg of the mixture of II and III, and it should generally be not less than 0.01 kg per kg of the mixture of II and III in order to achieve economic space/time yields.

Apart from the solid catalyst, the reaction is preferably carried out in the liquid phase, ie. both the starting substances II and III and the product should be virtually completely in the liquid phase. If one of the substances is solid under the reaction conditions, a solvent is also used, but if the substances are all liquid and miscible with one another, it is not necessary to use a solvent unless advantageous for other reasons, for example because the starting substances are already available in dissolved form or because working up is thereby simplified.

Suitable solvents are inert liquids, for example chlorinated hydrocarbons, eg. methylene chloride, aromatic hydrocarbons, eg. toluene, ethers, eg. tetrahydrofuran and dioxane, and $C_1$-$C_4$-alcohols which do not give rise to any noticeable degree of trans-esterification (X and Y are —$COOR^2$).

The reaction is preferably carried out under an $H_2$ pressure range of from 1 to 50 bar at from 25° to 180° C., usually under an $H_2$ pressure of from 1 to 10 bar and at 50° to 150° C., depending on the reactivity of the starting compounds II and III.

Equimolar amounts of II and III are advantageously used. If II is present in excess, self-condensation of the excess amount is to be observed in certain circumstances, and if III is present in excess, two adduct formations with II can take place, with elimination of water.

However, observations have so far shown that the side reactions caused by the presence of water or an excess of one of the starting substances are of minor significance, since the main reaction (adduct formation of II with III, followed by dehydration and hydrogenation) proceeds more rapidly than the side reactions. It should therefore merely be ensured that the times for the main reaction are not substantially exceeded, which, needless to say, is self-evident.

The process according to the invention can be carried out continuously or batchwise in a conventional manner and in principle does not depend on the nature of the starting compounds II and III.

Examples of aldehydes II are:

aliphatic aldehydes of 1 to 20 carbon atoms, especially $C_1$-$C_{20}$-alkanals; formaldehyde is advantageously used in the solid polymeric form, for example as paraformaldehyde;

cycloaliphatic aldehydes which are derived from 5-membered or 6-membered cyclic compounds;

araliphatic aldehydes, eg. phenylacetaldehyde;

isocyclic aromatic aldehydes which are derived from benzene or more highly fused ring systems thereof; and heterocyclic aromatic aldehydes, eg. the pyridinealdehydes or the thiophenealdehydes.

These aldehydes may contain substituents, eg. halogen, cyano, nitro or disubstituted amino, and heteroatoms or groupings, eg. oxygen, sulfur or —CO—O—.

If the aldehydes contain reactive groups or groupings, these may be modified under certain circumstances, but without affecting the principle of the reaction according to the invention. Thus, an unsaturated aldehyde, eg. acrolein or a derivative I of this aldehyde, may be hydrogenated, but it is possible to promote or suppress the hydrogenation by conventional hydrogenation techniques. The character of an unsaturated radical $R^1$ is, however, generally retained because the double bond formed by the condensation reaction is greatly activated by X and Y and is therefore preferentially hydrogenated.

The reaction principle of course also applies to polyvalent aldehydes, eg. to terephthalaldehyde, providing interesting possibilities for the synthesis of compounds I containing two or more —CH(X)Y groupings in the molecule.

Compounds III, of which the characteristic feature is the activated methylene group between X and Y, include:

$C_1$-$C_{10}$-alkyl esters of malonic acid, especially the methyl and ethyl ester, esters of acetoacetic acid, especially $C_1$-$C_{10}$-alkyl esters, preferably the methyl and ethyl ester, acetylacetone and higher homologs thereof where the acyl radical is of not more than 10 carbon atoms, $C_1$-$C_{10}$-alkyl esters of cyanoacetic acid, especially the methyl and ethyl ester, acylacetic acid nitriles where acyl is of not more than 10 carbon atoms, especially acetoacetonitrile, and malodinitrile.

Compounds III with a —CO—$CH_2$—CO— grouping in which the acyl groups are linked to form a ring, as in cyclopentane-1,3-dione, are also suitable.

The process according to the invention substantially simplifies synthesis of the compounds I, which are used as intermediates for other syntheses, especially for those of drugs. Thus, the ethyl n-butylcyanoacetate which can be obtained from n-butyraldehyde and ethyl cyanoacetate is an intermediate for the known analgesic phenylbutazone.

EXAMPLES

EXAMPLES A TO J

Preparation of various catalysts

In each case 100 g of a pulverulent material used as a condensation catalyst were mixed to a paste with 100 ml of aqueous palladium nitrate solution and cylindrical particles 2 mm in diameter and 5 mm in height were shaped from the paste. The particles were dried and heated at 500° C. under a hydrogen atmosphere for 6 hours, whereupon the Pd was reduced to the metal. The aqueous Pd nitrate solution always contained an amount of the salt corresponding to the composition of the catalyst.

Table 1 shows the characteristics of the catalysts thus prepared:

TABLE 1

| Catalyst | Condensing components [g] | Pd content % by weight |
|---|---|---|
| A | $\gamma$-$Al_2O_3$, 100 | 2.00 |
| B | " | 0.75 |
| C | " | 0.50 |
| D | " | 1.00 |
| E | $\gamma$-$Al_2O_3$, 95; $Pr_2O_3$, 5 | 0.75 |
| F | $CePO_4$, 100 | 0.50 |
| G | $Dy_2O_3$, 100 | 1.00 |
| H | ZnO, 100 | 0.50 |
| I | $Zn_3(PO_4)_3$, 100 | 0.50 |
| J | $\alpha$-$Al_2O_3$, 100 | 10.00 |

EXAMPLES 1 TO 18

Preparation of various compounds I

In each case a g of an aldehyde II, b. g of a compound III and c g of one of the catalysts A to J were heated at T°C under a hydrogen pressure of p bar in an autoclave for t hours. The amounts of a and b were always equimolar relative to one another. Conventional distillation working up of the reaction mixture which remained after removal of the catalyst and the water of reaction gave a yield of y% of the desired compound I.

The experimental conditions and results are summarized in Table 2.

TABLE 2

| Example | aldehyde II | [g] | compound III | [g] | cat. [g] | t [h] | p [bar] | T [°C.] | compound I B.p. [°C./mbar] | y [%] |
|---|---|---|---|---|---|---|---|---|---|---|
| 1 | n-butanal | 535 | ethyl cyanoacetate | 840 | A 40 | 7 | 20 | 70 | ethyl n-butyl-cyanoacetate 124–126/20 | 95 |
| 2 | propanal | 52.2 | acetylacetone | 90 | B 7 | 6 | 20 | 75 | 3-propylpentane 2,4-dione 102–110/20 | 93 |
| 3 | n-butanal | 50.4 | methyl acetoacetate | 81 | C 6 | 8 | 35 | 80 | methyl n-butyl-acetoacetate 102/10 | 92 |
| 4 | n-octanal | 256 | methyl acetoacetate | 232 | C 20 | 3 +3 | 15 25 | 70 80 | methyl n-octyl-acetoacetate 93–95/0.3 | 90 |
| 5 | 2-phenyl-propanal | 134 | ethyl cyanoacetate | 113 | D 20 | 2 +2 +2 | 20 35 45 | 50 90 130 | ethyl 2-cyano-4-phenylpentanoate; 128–132/0.2 | 85 |
| 6 | methoxy-acetaldehyde | 82 | ethyl cyanoacetate | 113 | B 10 | 2 +2 +2 | 15 20 25 | 50 75 100 | ethyl 2-cyano-4-methoxybutyrate 128–132/22 | 91 |
| 7 | paraformaldehyde | 150 | diethyl malonate | 800 | C 50 | 2 +2 +2 | 15 35 35 | 70 96 110 | diethyl methylmalonate 101–108/30 | 83 |
| 8 | iso-butanal | 57.6 | ethyl cyanoacetate | 90 | E 6 | 2 +2 +2 | 20 40 55 | 70 110 130 | ethyl 2-cyano-4-methylpentanoate; 135/22 | 90 |
| 9 | n-hexanal | 200 | diethyl malonate | 320 | E 25 | 2 +2 +2 | 25 45 55 | 70 110 130 | diethyl n-hexyl malonate 91–100/0.3 | 78 |
| 10 | acetaldehyde | 48.4 | ethyl cyanoacetate | 113 | C 20 | 6 | 50 | 40 | ethyl ethyl-cyanoacetate 50–60/0.3 | 70 |
| 11 | n-butanal | 720 | acetylacetone | 1000 | C 70 | 3 +3 | 30 35 | 70 80 | n-butylpentane-2,4-dione 100–105/28 | 89 |
| 12 | 3-formyl-pinane  | 332 | ethyl cyanoacetate | 226 | B 50 | 3 +3 | 35 40 | 70 75 | ethyl pin-3-yl methylcyanoacetate, 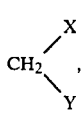 | 90 |
| 13 | propanal | 29 | malodinitrile | 33 | F 5 | 8 | 50 | 35 | n-propylmalodinitrile | 70 |
| 14 | n-butanal | 50.4 | methyl acetoacetate | 81 | G 6 | 8 | 35 | 80 | methyl n-butyl-acetoacetate | 80 |
| 15 | n-butanal | 535 | ethyl cyanoacetate | 840 | H 40 | 7 | 20 | 70 | ethyl n-butyl-cyanoacetate | 80 |
| 16 | n-butanal | 535 | ethyl cyanoacetate | 840 | I 40 | 7 | 20 | 70 | ethyl n-butyl-cyanoacetate | 82 |
| 17 | n-butanal | 535 | ethyl cyanoacetate | 840 | J 50 | 12 | 1 | 70 | ethyl n-butyl-cyanoacetate | 90 |
| 18 | propanal | 29 | cyclohexane-1,3-dione in 20 ml of methanol | 56 | C 3 | 10 | 40 | 60 | n-propylcyclo-hexane-2,6-dione | 75 |

We claim:

1. A process for the preparation of a compound of the formula I $$R^1-CH_2-CH\begin{matrix}X\\Y\end{matrix} \quad I$$

where $R^1$ is alkyl of 1–20 carbons and X and Y denote $-COOR^2$, or $-CN$ with $R^2$ being a $C_1-C_{10}$ alkyl, which process comprises:
 reacting an aldehyde II
$$R^1-CHO \quad II$$
with a compound III $$CH_2\begin{matrix}X\\Y\end{matrix},$$

wherein R', X and Y are as above defined, in the liquid phase at a temperature of from 25° to 180° C. in the presence of hydrogen, a noble metal hydrogenation catalyst and a condensation catalyst consisting essentially of an oxide or phosphate of magnesium, aluminum, titanium, zinc or a rare earth metal, said reaction taking place in the essential absence of a homogeneous catalyst component.

2. The process of claim 1, wherein a combined hydrogenation and condensation catalyst is employed which is obtained by mixing a pulverulent condensation catalyst with an aqueous solution of palladium to provide a paste, forming particles from the paste and drying the particles.

3. The process of claim 2, wherein the condensation catalyst is an oxide of aluminum and the combined catalyst particles are beads having a diameter of from 1 to 10 mm.

4. The process of claim 3, wherein $\gamma$-$Al_2$-$O_3$ or $\eta$-$Al_2O_3$ is used as the condensation catalyst.

5. A process as defined in claim 3 wherein a mixed catalyst of the material of the condensation catalyst and a noble metal of group VIII of the periodic table is used.

6. A process as defined in claim 2, wherein palladium is used as the noble metal.

7. A process as defined in claim 3 wherein $\gamma$-$Al_2O_3$ or $\eta$-$Al_2O_3$ is used as the condensation catalyst.

* * * * *